United States Patent [19]

Omori et al.

[11] 4,422,981
[45] Dec. 27, 1983

[54] PROCESS FOR PRODUCTION OF 2-METHYLENEGLUTARONITRILE

[75] Inventors: Hiroyuki Omori, Yokkaichi; Makoto Takeda, Ami; Koichi Fujita, Matsusaka; Mitsugi Kataoka, Yokkaichi, all of Japan

[73] Assignee: Mitsubishi Petrochemical Company Limited, Tokyo, Japan

[21] Appl. No.: 361,379

[22] Filed: Mar. 24, 1982

[30] Foreign Application Priority Data

Mar. 25, 1981 [JP] Japan .................................. 56-43715

[51] Int. Cl.[3] ..................... C07C 121/20; C07C 120.00
[52] U.S. Cl. ...................... 260/465.8 D; 260/465.8 R; 203/77; 203/91; 203/DIG. 3
[58] Field of Search ................. 260/465.8 D, 465.8 R; 203/91, 77, DIG. 3

[56] References Cited

U.S. PATENT DOCUMENTS

| 3,644,476 | 2/1972 | Onsager | 260/465.8 D |
|---|---|---|---|
| 3,644,477 | 2/1972 | Onsager | 260/465.8 D |
| 3,671,567 | 6/1972 | Onsager | 260/465.8 D |
| 3,671,568 | 6/1972 | Onsager | 260/465.8 D |
| 3,733,351 | 5/1973 | Watanabe et al. | 260/465.8 D |
| 4,100,186 | 7/1978 | Wright | 260/465.8 D |
| 4,102,915 | 7/1978 | Jennings et al. | 260/465.8 D |
| 4,263,224 | 4/1981 | Jennings et al. | 260/465.8 D |
| 4,316,857 | 2/1982 | Gilbert | 260/465.8 D |

OTHER PUBLICATIONS

Kirk-Othmer, "Encyclopedia of Chemical Technology", Vol. 1, (1963), pp. 348 and 349.

Primary Examiner—Joseph Paul Brust
Attorney, Agent, or Firm—Oblon, Fisher, Spivak, McClelland & Maier

[57] ABSTRACT

From an acrylonitrile-dimerization liquid product prepared by contacting acrylonitrile with a specific catalyst composed of a metal halide and a trialkylamine, 2-methyleneglutaronitrile is efficiently recovered by a process which comprises contacting the reaction liquid product under stirring with benzene, toluene or xylene as well as with water in specific ratios, and then separating the resulting aromatic hydrocarbon layer from the mixture to recover 2-methyleneglutaronitrile.

11 Claims, 3 Drawing Figures

PROCESS FOR PRODUCTION OF 2-METHYLENEGLUTARONITRILE

BACKGROUND OF THE INVENTION

This invention relates to a process for producing 2-methyleneglutaronitrile (hereinafter sometimes referred to as MGN) by liquid phase-dimerization of acrylonitrile (hereinafter sometimes referred to as AN). More particularly, this invention relates to a process for recovering MGN efficiently from the liquid dimerization product.

Hitherto, a process for preparation of MGN comprising contacting AN in liquid phase with a catalyst composed of a metal halide and a trialkylamine has been known. According to this process, an MGN solution is obtained, but the MGN cannot always be recovered readily from the resulting liquid reaction product.

Distillation methods may be used to recover MGN from the liquid reaction product. However, MGN itself is a readily polymerizable compound, and, moreover, the polymerization of MGN readily occurs when it is heated in the presence of a catalyst for the synthesis of MGN. Thus, the recovery of MGN by distillation is very low, and, moreover, formation of MGN polymers causes trouble in the operation of apparatus. Therefore, such a distillation method is not practical on a commercial scale.

It may be readily anticipated that the problems of the marked polymerization in the case of recovering MGN by distillation from the reaction liquid product can be solved to some extent by deactivating or removing the remaining catalyst. Accordingly, a method has been proposed which comprises deactivating the remaining catalyst by treating the reaction product with an aqueous acid solution or an aqueous alkali solution, transferring it to the aqueous layer, and then separating the aqueous layer by stationary separation. According to this method, however, separation of the aqueous layer from the oily layer is very difficult because an emulsion forms, and, moreover, the separation operation is very complicated because lumps of polymer form. In addition, the treatment of the drainage water containing a metal halide and a halogen is also required. Thus this method is very troublesome as a commercial process.

SUMMARY OF THE INVENTION

An object of the present invention is to solve the above described problems. This object has been achieved in this invention by treating MGN with a specific extraction solvent and a small quantity of water, which are used in combination.

In accordance with the present invention, there is provided, in the preparation of 2-methyleneglutaronitrile which comprises dimerization of acrylonitrile by contacting acrylonitrile in a liquid phase with a catalyst composed of a trialkylamine and a metal halide represented by the general formula $MeX_n$ wherein: Me stands for aluminum, titanium, vanadium, iron, cobalt or zinc; X stands for a halogen; and n is an integer equal to the valence of the metal Me, a process characterized by the steps of contacting the resulting reaction liquid product under agitation with an aromatic hydrocarbon selected from benzene, toluene and xylene as well as water, and then separating the resulting aromatic hydrocarbon layer from the mixture to obtain 2-methyleneglutaronitrile, the quantities of the aromatic hydrocarbon and water being, respectively, 1 to 50 fold by weight and 1 to 10 percent by weight relative to that of the reaction liquid product.

When the AN-dimerization liquid product is subjected to extraction with an extraction solvent selected from aromatic hydrocarbons such as benzene, MGN moves to the upper extraction solvent layer, and polymeric materials and catalyst component descend to the lower layer. Thus the extraction solvent layer is separated, and MGN can be readily recovered therefrom. It may be said that this selective extractability possessed by the specific aromatic hydrocarbon was totally unexpected.

The most unique and unexpected effect in the present invention is the dissolution of the precipitates in the lower layer by the water used together with the aromatic hydrocarbon. More specifically, we have had a knowledge that the polymeric material and catalyst component which precipitate in the lower layer when the AN-dimerization liquid product is extracted with the specific aromatic hydrocarbon are then solidified into rigid resinous materials and deposited on the bottom of a stationary separation vessel. It is difficult to draw out the deposited material, which is not readily dispersed even by agitation. We have further found that the solidification of the polymeric material and the like can be prevented by the presence of a small quantity of water in the course of the extraction treatment. Such behavior by water was totally unexpected. In this connection, because the amount of water used in this case is small, the above-mentioned problem accompanying the treatment of drainage water is substantially reduced.

DETAILED DESCRIPTION OF THE INVENTION

1. Catalytic Dimerization of AN

Figure 1:
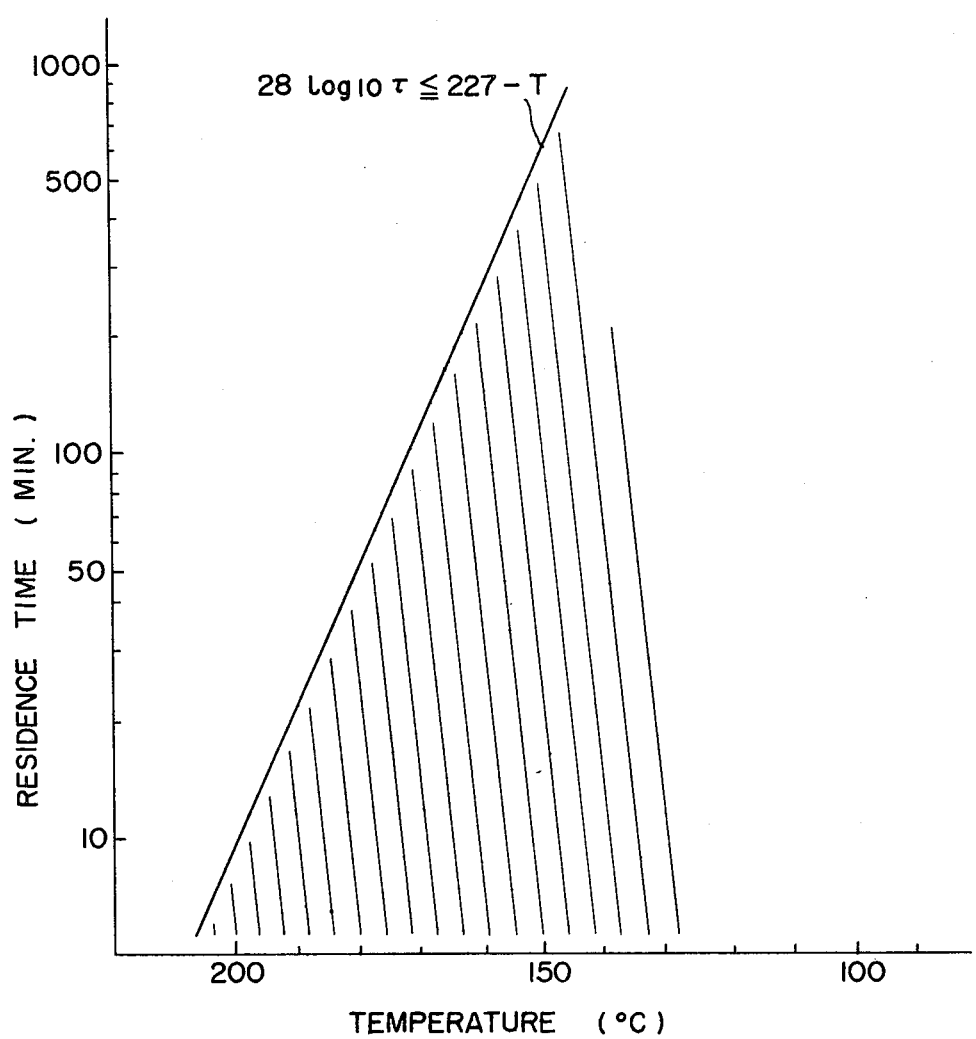
FIG. 1 is a graph of temperature versus residence time indicating the distillation conditions under which there is almost no formation of a polymeric material.

A process for preparation of MGN which comprises contacting acrylonitrile with a catalyst composed of a metal halide and a trialkylamine in a liquid phase to dimerize acrylonitrile has been known (e.g., as disclosed in Japanese Patent Publication No. 6892/71, No. 15492/71 and No. 8287/72).

The metal halide, constituting one component of the catalyst, is represented by the general formula $MeX_n$, wherein Me stands for aluminum, titanium, vanadium, iron, cobalt or zinc, X stands for a halogen, and n represents the valence of the metal Me. Examples of such metal halides are aluminum trichloride, aluminum triiodide, titanium trichloride, titanium tetrachloride, titanium tetrabromide, vanadium tribromide, titanium tetraiodide, ferrous chloride, ferrous bromide, ferrous iodide, cobalt chloride, cobalt bromide, cobalt iodide, zinc chloride, zinc bromide, and zinc iodide. Of these halides, the chlorides and especially zinc chloride are preferred. These halides can be used in combination with each other.

The other component of the catalyst is a trialkylamine. The alkyl groups can be the same or different from each other. Each of the alkyl groups preferably does not have more than 8 carbon atoms. Examples of such trialkylamines are trimethylamine, triethylamine, tripropylamines, tri-n-butylamine, triisobutylamine trihexylamines, and trioctylamines. Among these, lower trialkylamines and especially triethylamine are preferred. These trialkylamines can be used in combination.

The above described two components are used generally in an amine/metal halide molar ratio of 0.1 to 20, preferably in the molar ratio of 0.5 to 10, and most preferably in the molar ratio of 1 to 5. When the molar ratio is over 20, the yield of MGN to the resulting catalyst is lowered. On the other hand, when the molar ratio is less than 0.1, the reaction velocity substantially decreases. Thus the above-mentioned ranges are defined. The catalyst is used in a quantity such that the metal halide is not less than 0.5% by weight of the AN, preferably in the range of 2 to 10% by weight of the AN.

The dimerization of AN in the liquid phase can be carried out in any manner that ensures the contact between the catalyst system composed of the above-mentioned two components and the AN. A reaction solvent is not especially required unless it is used for a special purpose. The above-mentioned catalyst components can be added to the AN, separately or as a mixture. The reaction temperature and pressure can be in optional ranges that maintain the AN in liquid phase but it is generally preferred that the temperature be in the range of 0° to 70° C. and the pressure be atmospheric pressure.

2. Extraction of MGN (1) Material subjected to extraction

The reaction liquid product obtained from the above-described reaction is subjected to an extraction treatment. When no reaction solvent is used, the MGN concentration in the resulting reaction liquid product is in a range of the order of 45 to 76% by weight.

In a preferred embodiment of the present invention, the reaction liquid is pretreated and then subjected to the extraction. In the pretreatment, low-boiling materials such as unreacted AN and the trialkylamine used as a catalyst component and a solvent used optionally (having a lower boiling point than MGN) are distilled off preferably under a reduced pressure. If such unreacted AN and the like is not removed prior to the extraction, a larger quantity of the extraction solvent is required.

(2) Extraction solvent and extraction

The extraction solvent to be used in the present invention is benzene, toluene or xylenes (hereinafter sometimes referred to as BTX), of which toluene is especially preferred.

When BTX is added to the liquid product of the AN dimerization (preferably the liquid from which AN and the trialkylamine have been removed), MGN moves to the BTX layer, and polymeric materials and the catalyst components descend to the lower layer. The BTX layer is separated and MGN is recovered therefrom.

The quantity of the BTX to be used is 1 to 50-fold by weight and preferably 2 to 5-fold by weight that of the reaction liquid product (when unreacted AN and the trialkylamine have been distilled off, the amount of reaction liquid product before the distillation step). When the BTX is used in a quantity less than 1-fold by weight that of the liquid product, sufficient extraction cannot be achieved. Even if the quantity of the BTX is over 50-fold by weight, the resulting extraction efficiency cannot be further enhanced, and the recovery of MGN from the extract is disadvantageous.

The extraction is normally carried out by contacting the reaction liquid product with the extraction solvent under a suitable agitation conditions at 20° to 70° C., preferably at 30° to 50° C. In general, the quantity of the BTX used becomes less at a higher temperature.

The dimerization of AN may be carried out in the presence of a reaction solvent. A BTX can be used as the reaction solvent (c.f. the above-cited Japanese Patent Publication No. 6892/71). In this case, therefore, the extraction with BTX of the dimerization liquid product can be said to have also been accomplished in the course of the reaction. The present invention is intended to also include such an embodiment thereof.

(3) Treatment with water

In the present invention, the above described extraction with BTX is carried out in the presence of water. Water is added at the same time as the addition of BTX (not before the addition of BTX) or after the addition of BTX with agitation to maintain a solidifiable polymer in a liquid state.

The quantity of water to be used should be 1 to 10% by weight, preferably 2 to 6% by weight, of the reaction liquid product (when unreacted AN and the trialkylamine have been distilled off, the quantity of the reaction liquid product before the distillation step). When the quantity of water is less, polymers form red-brown lumps which are difficult to take out. If the amount of water is greater, yellow viscous materials will be formed which will cause clogging in standing vessels and draw-off pipes.

(4) Separation of BTX layer and recovery of MGN

Separation of the MGN-containing BTX layer obtained as an upper layer after the extraction with BTX and recovery of MGN from the BTX layer can be conducted, for example, by separation thereof by decantation of a formed upper layer and distillation under a reduced pressure, or by other appropriate procedures.

We have found that the MGN in which the above mentioned catalyst remains unseparated and from which unreacted AN and the like have been removed undergoes marked polymerization upon heating, whereas the MGN treated according to the present invention is caused to have a markedly smaller thermal polymerization liability. However, since MGN is a compound having an ethylenically unsaturated bond, polymerization and solidification of the MGN obtained by this invention upon heating still cannot be avoided. Accordingly, upon obtaining MGN by distillation of the MGN from the BTX extract, it is desirable to prevent polymerization of the MGN by some measure.

A suitable polymerization inhibitor has been generally added to a polymerizable compound when it is subjected to distillation. However, a polymerization inhibitor which is fully effective for the distillation of crude MGN to be treated in the present invention has not yet been found. When such polymerizable materials are subjected to distillation, not only is a large amount of the material lost because of polymerization thereof, but the resulting distillation still residue fails to maintain its fluidity because of the increase in viscosity due to polymerization, which results in failure of the distillation operation. To prevent high-viscosity due to polymerization of the still residue, it may be possible to leave unrecovered a portion of the product monomer, which is a good solvent for the polymerized product, to maintain the fluidity of the still residue, but the loss of the product is not negligible. On the other hand, distillation of such heat-polymerizable materials should be conducted at a low temperature under reduced pressure, but it is necessary to fully investigate the polymerization properties of the material for setting a suitable temperature range for the distillation.

We have found that formation of the polymer is substantially negligible in the case where the crude MGN which has been obtained by treatment according to the present invention and then by removal of the BTX used is distilled under the temperature-time conditions given in the region indicated by the shaded portion of FIG. 1, for example, under the conditions of 10 hours or less at 150° C. or lower, 2 hours or less at 170° C. or lower, 30 minutes or less at 185° C. or lower or 10 minutes or less at 200° C. or lower. In other words, the distillation of the crude MGN to obtain MGN should be carried out in a distiller having a residence time of $\tau$ (minutes) at a temperature of T (°C.) satisfying the following requirement:

$$T \leq 227 - 28 \log_{10} \tau$$

It is preferable that the following requirement is satisfied:

$$70 \leq T \leq 200 - 28 \log_{10} \tau$$

When the distiller has a temperature range, the above requirement should preferably be satisfied at each temperature and also with respect to the integration of the residence time at respective temperatures. It is to be noted that the above temperature-residence time relationship indicates only the conditions of heating the liquid to be distilled, and does not necessarily restrict the boiling point in the distilling operation.

Figure 2:
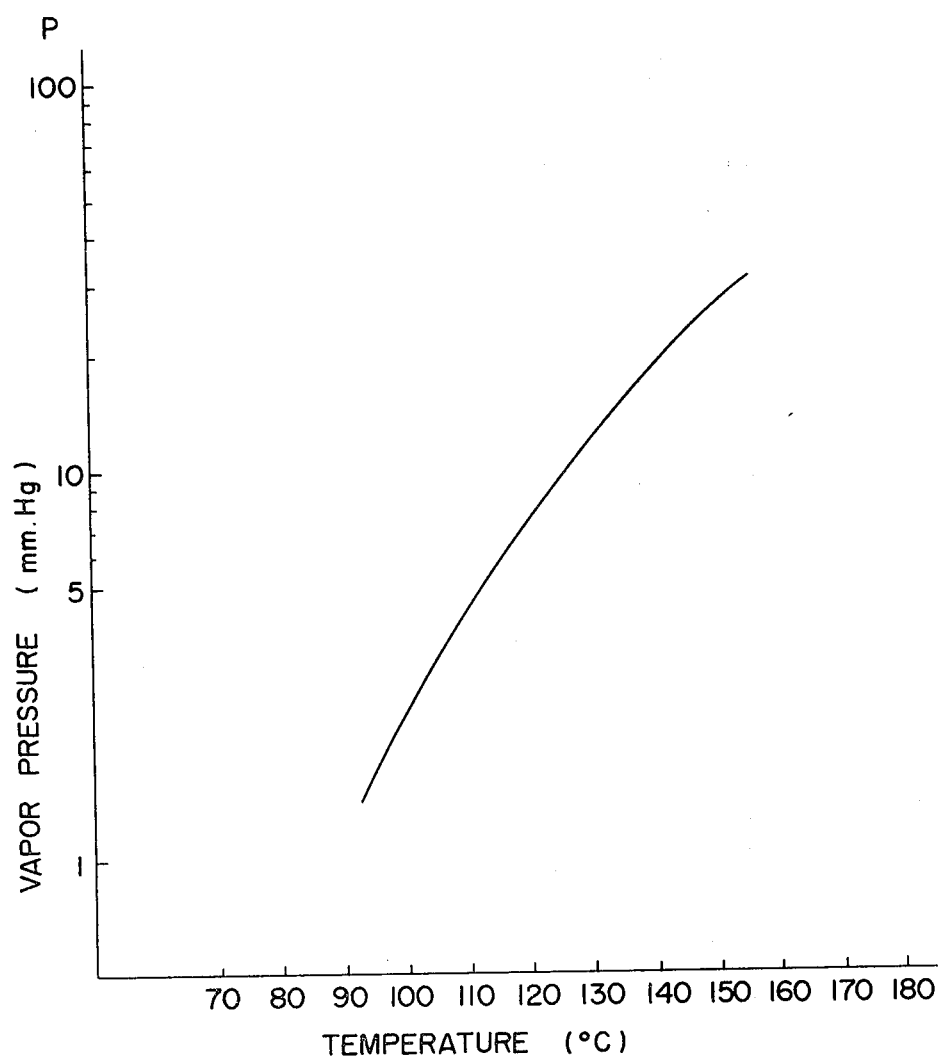
FIG. 2 is graph indicating the vapor pressure-temperature curve of MGN.

FIG. 2 shows the vapor pressure curve of MGN.

One of the preferred modes of practice to realize such temperature-time relations is to employ the liquid film evaporation method those of the falling film type and the centrifugal type in the distillation of the crude MGN to purify MGN. For example, in the falling film evaporation method, the crude MGN is caused to fall down, after or while being heated, in a thin film state in a distiller, during which MGN is evaporated off to leave heavy end. By this method, it is possible to hold the liquid-heating time to a few seconds to a few minutes. The liquid film evaporation methods can also be used effectively for distilling off the unreacted AN and amine from the dimerization reaction liquid product. Moreover, the evaporation methods can also be applied to distilling off the BTX from the BTX extract.

(5) Flow sheet

Figure 3:
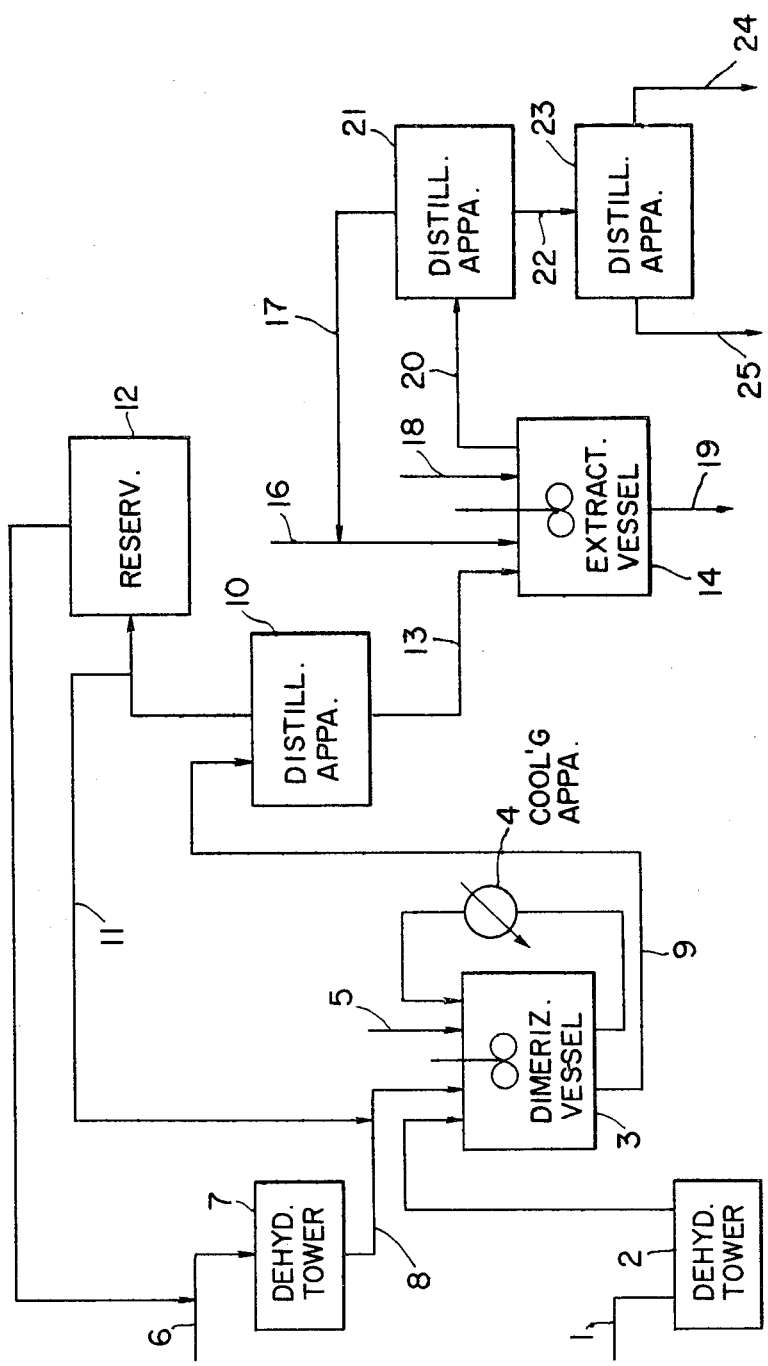
FIG. 3 is a flow sheet showing essential apparatus for carrying out one example of the preferred mode of the present invention.

FIG. 3 is a flow sheet showing essential apparatus for one example of preferred mode of practice of the present invention.

In FIG. 3, the starting material AN is supplied via a line 1, dehydrated sufficiently through a molecular sieve-packed dehydration tower 2, and then introduced into a dimerization reaction vessel 3. If desired, the AN is cooled prior to reaction to a specific temperature by a cooling apparatus 4. Then a specific quantity of an anhydrous metal halide is supplied via a line 5. A trialkylamine is supplied via a line 6, dehydrated sufficiently through a molecular sieve-packed dehydration tower 7, and then is added dropwise via a line 8 to the AN in the reaction vessel 3 under stirring. The reaction temperature is preferably in the range of 0° to 70° C. For controlling the reaction temperature to a specific temperature, the rate of addition of the trialkylamine is regulated and the reaction liquid is cooled by the cooling apparatus 4.

After the reaction has been carried out for a specific period of time, unreacted AN and the trialkylamine are recovered at a distillation apparatus 10 via a line 9. The recovered unreacted AN-containing trialkylamine can be reused as a reaction material via a line 11. The AN-amine mixture can be stored, depending on the necessity, in a reservoir 12 and used as a starting material when necessary. Because the mixture shows white turbidity when stored as it is, a small quantity (for example, about 0.3 to 0.5% by weight) of water is added to the mixture. The resulting aqueous mixture can be stored for a long period at a temperature of 30° C. or lower and reused. The AN-amine mixture can be stored more safely by adding thereto both water and 10 to 100 ppm of a polymerization inhibitor such as hydroquinone monomethyl ether, but the addition of only a polymerization inhibitor without water is not desirable.

The bottom liquid supplied from the distillation apparatus 10 is introduced via a line 13 to an extraction vessel 14, and then a specific quantity of BTX such as toluene is added thereto via a line 16 (and a line 17). After agitation, a specific quantity of water is added thereto via a line 18, and the mixture is allowed to stand. In this case, it is preferable to add the water in a dispersed or, more preferably, sprayed state before precipitates in the toluene solution descend.

The high-density product in the lower layer is taken out through a line 19, and the upper toluene solution layer is sent via a line 20 to a distillation apparatus 21 to recover the toluene. The recovered toluene is reusable via a line 17. The MGN from which toluene has been recovered is sent via a line 22 to a distillation apparatus 23, and is purified and obtained via a line 24. High-boiling impurities are discharged via a line 25.

In case the whole system is operated batchwise, it is possible to use a single distillation apparatus for all the operations carried out in the apparatus 10, 21 and 23 according to the above explanation.

3. Examples of Experiments

In order to indicate more fully the nature and utility of the present invention, the following specific examples of practice are set forth, it being understood that these examples are presented as illustrative only and are not intended to limit the scope of the invention.

EXAMPLE 1

(Synthesis)

A 3-liter glass lined autoclave was charged with 1,260 g of AN and 60 g of anhydrous zinc chloride. This step was followed by the addition thereto of 240 g of triethylamine. The mixture was subjected to reaction at 25° to 30° C. for 25 hours. By gas-chromatographic analysis of the resulting reaction liquid, it was found that the content of MGN was 64% and that the balance consisted essentially of triethylamine and the trimer or higher polymers of AN.

EXAMPLE 2

(Removal of unreacted AN, etc.)

Unreacted AN and triethylamine were distilled off under a reduced pressure of 105 Torr in a thin-film type distiller from the reaction liquid produced in Example 1, to obtain crude catalyst-containing MGN. By gas-chromatographic analysis, polymerization loss of MGN was found to be 1%.

EXAMPLE 3

(Extraction)

Four hundred (400) g of the crude catalyst-containing MGN obtained in Example 2 and 400 g of toluene were mixed, and then 20 g of water was added. The mixture was stirred at 50° C. for 30 minutes and then subjected to stationary separation. Thus 760 g of an oily phase consisting essentially of MGN and toluene in the upper layer and 60 g of high-density liquid consisting essentially of polymers, the metal salt and water in the lower layer were obtained. The lower layer was in a liquid state and readily separated from the oily phase.

EXAMPLE 4

(Reference)

Crude MGN produced by recovering toluene from the toluene phase obtained in Example 3 was heated to 185° C., whereupon polymerization of 5% occurred in 30 minutes, and 18% of a polymer was formed in 60 minutes. When the crude MGN was heated to 170° C., a polymer was produced in a quantity of 2% in 30 minutes and 15% in 100 minutes. When it was heated to 150° C., no formation of a polymer was observed in 60 minutes.

EXAMPLE 5

(Reference)

The crude MGN produced by recovering toluene from the oily phase obtained in Example 3 was distilled under a reduced pressure of 1.4 Torr in a thin-film distiller. MGN having a purity of 99.4% was recovered in a yield of 99%. The viscosity of the distillation residue was 50 cp at 98.9° C. In the distillation operation, the heating temperature was 147° C., and the average residence time of the liquid was 6 minutes.

EXAMPLE 6

(Comparative)

The crude catalyst-containing MGN obtained in Example 2 was heated to 150° C., and a polymer was produced in a quantity of about 50% in 60 minutes.

What is claimed is:

1. In a process for production of 2-methyleneglutaronitrile by the dimerization of substantially anhydrous acrylonitrile by contacting said acrylonitrile in a liquid phase with a catalyst composed of a trialkylamine and a metal halide of the formula $MeX_n$, wherein Me represents aluminum, titanium, vanadium, iron, cobalt or zinc; X is chlorine, bromine or iodine; and n is an integer equal to the valence of the metal Me, the improvement comprising the steps of:

(a) contacting the resulting liquid reaction product while being agitated with an aromatic hydrocarbon selected from the group consisting of benzene, toluene and xylene and added water;

(b) separating the resulting aromatic hydrocarbon phase from the mixture; and (c) recovering 2-methyleneglutaronitrile from the aromatic hydrocarbon phase, the quantities of the aromatic hydrocarbon and the water being, respectively, 1 to 50-fold by weight and 1 to 10% by weight relative to the amount of liquid reaction product, said water being added to effect the contact step no earlier than the contact of the liquid reaction product with said aromatic hydrocarbon thereby forming a mass which comprises the catalyst component and a polymeric material which precipitates when the mass is not agitated.

2. The process of claim 1, wherein the unreacted acrylonitrile and trialkylamine are recovered from the liquid reaction product by distillation, and subsequently the liquid reaction product is contacted with the aromatic hydrocarbon-water combination.

3. The process of claim 1, wherein said liquid reaction product is simultaneously contacted with both the aromatic hydrocarbon and water.

4. The process of claim 1, wherein the liquid reaction product is first contacted with the aromatic hydrocarbon and subsequently with water while the mixture is being agitated.

5. The process of claim 1, wherein said liquid reaction product is contacted with the aromatic hydrocarbon and water at a temperature of 20° to 70° C.

6. The process of claim 1, wherein the aromatic hydrocarbon phase is separated from said mixture by stationary separation.

7. The process of claim 1, wherein the aromatic hydrocarbon phase is subjected to distillation under reduced pressure thereby resulting in the removal of the aromatic hydrocarbon by distillation leaving crude 2-methyleneglutaronitrile.

8. The process of claim 7, wherein said crude 2-methyleneglutaronitrile is purified by distillation under reduced pressure.

9. The process of claim 8, wherein said distillation is conducted so that said crude 2-methyleneglutaronitrile will be removed by distillation after being kept at a temperature of T (°C.) for a residence time of $\tau$ (minutes) wherein the values of T and $\tau$ satisfy the requirement:

$$T \leq 227 - 28 \log_{10} \tau$$

10. The process of claim 8, wherein said crude 2-methyleneglutaronitrile is distilled from the crude product by the liquid film evaporation technique.

11. The process of claim 1, wherein said metal halide is a metal chloride and said trialkylamine is triethylamine.

* * * * *